United States Patent [19]
Kuroda et al.

[11] Patent Number: 5,605,459
[45] Date of Patent: Feb. 25, 1997

[54] METHOD OF AND APPARATUS FOR MAKING A DENTAL SET-UP MODEL

[75] Inventors: Takayuki Kuroda, Yokohama; Nobuyoshi Motohashi, Musashino; Mutsushi Muramoto, Osaka, all of Japan

[73] Assignees: Unisn Incorporated, Osaka; Takayuki Kuroda, Kanagawa, both of Japan

[21] Appl. No.: 522,458

[22] Filed: Aug. 31, 1995

[30] Foreign Application Priority Data

Apr. 14, 1995 [JP] Japan .................................. 7-113790

[51] Int. Cl.$^6$ ........................... A61C 9/00; A61C 11/00; A61C 19/04
[52] U.S. Cl. ............................ 433/214; 433/213; 433/68
[58] Field of Search ........................... 433/214, 213, 433/68, 72, 196, 229

[56] References Cited

U.S. PATENT DOCUMENTS

| | | | |
|---|---|---|---|
| 4,610,629 | 9/1986 | Schrems et al. | 433/213 |
| 4,611,288 | 9/1986 | Duret et al. | 433/213 |
| 4,663,720 | 5/1987 | Duret et al. | 433/214 |
| 4,742,464 | 5/1988 | Duret et al. | 433/214 |
| 4,935,635 | 6/1990 | O'Harra | 433/214 |
| 4,964,770 | 10/1990 | Steinbichler et al. | 433/214 |
| 5,092,022 | 3/1992 | Duret | 433/213 |
| 5,413,481 | 5/1995 | Goppel et al. | 433/214 |

*Primary Examiner*—Gene Mancene
*Assistant Examiner*—Jinan Glasgow
*Attorney, Agent, or Firm*—Hamilton, Brook, Smith & Reynolds, P.C.

[57] ABSTRACT

A method of and an apparatus for making a dental set-up model utilizable in the practice of orthodontics and, more particularly, to facilitation of making the dental set-up model. The shape of an impression which is a replica of dental teeth and dental alveolar ridges of a patient is first converted on a non-contact basis into electronic data by means of a three-dimensional profile analyzer utilizing an irradiation beam. Using this electronic data and within the framework of such electronic data, representative plane defined by anatomically proximal contact points A1, anatomically distal contact points A2 and an intermediate point E between the bucco-cervical point B1 and the lingo-cervical point B2 are formed by cutting out the individual teeth. Subsequently, for each tooth, a DI line, which is a straight line connecting between the bucco-cervical point B1 and a representative point C of a cusp or edge that has been projected onto the representative plane, and a DH line intersecting the DI line perpendicularly at a point spaced a predetermined distance from the representative point C towards the dental alveolar ridge are formed. Then, the DH lines for the respective teeth are arranged on a plane along a guide line descriptive of an ideal individual dental arch form and respective heights of the DH lines for all teeth which have been lined up to a predetermined height are adjusted to a predetermined level, followed by adjustment of the angle of inclination of the representative plane for each tooth relative to a facial reference line set up on the face.

11 Claims, 11 Drawing Sheets

POSTERIOR PLANE

FIG. 4 h VALUE (UNIT:mm)

| Tooth Number | MANDIBLE(Lower) | | MAXILLA(Upper) | |
|---|---|---|---|---|
| | Left | Right | Left | Right |
| 1 | 3.0 | 3.0 | 3.0 | 3.0 |
| 2 | 2.0 | 2.0 | 2.0 | 2.0 |
| 3 | 2.0 | 2.0 | 2.0 | 2.0 |
| 4 | 2.5 | 2.5 | 2.5 | 2.5 |
| 5 | 2.5 | 2.5 | 2.5 | 2.5 |
| 6 | 2.0 | 2.0 | 2.0 | 2.0 |
| 7 | 2.0 | 2.0 | 2.0 | 2.0 |

METHOD OF AND APPARATUS FOR MAKING A DENTAL SET-UP MODEL

BACKGROUND OF THE INVENTION

1. Field of the Invention

The present invention relates to a method of and an apparatus for making a dental set-up model utilizable in the practice of orthodontics and, more particularly, to facilitation of making the dental set-up model.

2. Description of the Prior Art

In general, in the practice of orthodontics or any other dental treatment including preparation of a denture, a dental set-up model is often prepared based on an impression model representative of the dentition and the alveolar ridge of a patient to be orthodontically treated. This set-up model is generally prepared by cutting and arranging individual teeth on the alveolar ridge of the impression model. With this set-up model so prepared, not only is a final goal for the dental treatment made clear, but also the occlusal condition between the maxillary and the mandibular dentitions can be ascertained specifically.

Also, the patient when the dental set-up model is presented can visually ascertain the possible final result of orthodontic treatment he or she will receive and, therefore, the dental set-up model is a convenient tool in terms of psychological aspects of the patient.

However, since according to the prior art making the set-up model is carried out manually, involving not only a substantial amount of labor required, but also a substantial amount of time required. Also, where a number of treatments for accomplishing the orthodontic objective are available, the job of making the set-up model tends to become complicated and, therefore, reduction in time required to exercise this job and elimination of labor have hitherto been desired.

SUMMARY OF THE INVENTION

Accordingly, the present invention has been devised to substantially eliminate the foregoing problems and is to provide an in, proved method of and an improved apparatus which are easily practiced to make the dental set-up model.

In order to accomplish the foregoing and other objects and features of the present invention, the shape of an impression which is a replica of dental teeth and dental alveolar ridges of a patient is first convened on a non-contact basis into electronic data by means of a three-dimensional profile analyzer utilizing an irradiation beam. Using this electronic data and within the framework of such electronic data, the individual teeth are cut out and representative plane deformed by anatomically proximal contact points A 1, anatomically distal contact points A2 and an intermediate point E between the bucco-cervical point B1 and the lingo-cervical point B2 are formed. Subsequently, for each tooth, a DI line, which is a straight line connecting between the bucco-cervical point B1 and a representative point C of a cusp or edge that has been projected onto the representative plane, and a DH line intersecting the DI line perpendicularly at a point spaced a predetermined distance from the representative point C towards the dental alveolar ridge are formed. Then, the DH lines for the respective teeth are arranged on a plane along a guide line descriptive of an ideal individual dental arch form and respective heights of the DH lines for all teeth which have been lined up to a predetermined height are adjusted to a predetermined level, followed by adjustment of the angle of inclination of the representative plane for each tooth relative to a facial reference line set up on the face.

If required, a maxillary occlusal plane defined by a position of the representative point C of maxillary anterior teeth and a position of the representative point C of left and fight maxillary first molars and, also, a mandibular occlusal plane defined by a position of the representative point C of mandibular anterior teeth and a position of the representative point C of left and right mandibular first molars may be determined. Based on the occlusal plane so determined between the maxillary and mandibular dentitions, the height of the DH line for each tooth or an angle of inclination of the representative plane for each tooth may be modified.

If required, at least one of the position of the representative point C of the maxillary anterior teeth and the position of the representative C of the mandibular anterior teeth is adjusted so that a predetermined over-jet value and an over-bite value can be secured between the maxillary and mandibular anterior teeth. Then the maxillary occlusal plane is defined by the adjusted position of the representative point C of the maxillary anterior teeth and the position of the representative point C of the maxillary left and right first molars, the profile of which has been acquired., and the mandibular occlusal plane is defined by the adjusted position of the representative point C of the mandibular anterior teeth and the position of the representative point C of the mandibular left and right first molars, the profile of which has been acquired. Then, based on the determined maxillary and mandibular occlusal planes, the height of the DH line for each tooth or the angle of inclination of the representative plane for each tooth is modified.

Also if desired, a displacement on the dental alveolar ridge between the representative point of each tooth including said points A1, A2, B1 and B2 or C and a reference line of each tooth of said DI or DH line may be calculated.

Again if desired, the three-dimensional shape may be imparted to each of the teeth arranged on the DH lines to thereby form an arrangement of the three-dimensional profile. Then, after the maxillary and mandibular dentitions having the three-dimensional profile have been allowed to bite and the resultant occlusal condition has been confirmed in reference to the area of contact between the maxillary and mandibular teeth, the mandibular dental arch may be moved to establish a proper occlusal relationship between the maxillary and mandibular teeth and, at the same time, the amount of such movement may be calculated.

According to the present invention, for each tooth and within the framework of the electronic data, the representative plane defined by the anatomically proximal contact points A1, the anatomically distal contact points A2 and the intermediate point E between the bucco-cervical point B1 and the lingo-cervical point B2 are formed, followed by formation of the DI line, which is a straight line connecting between the bucco-cervical point B1 and a representative point C of a cusp or edge that has been projected onto the representative plane, and a DH line intersecting the DI line perpendicularly at a point spaced a predetermined distance from the representative point C towards the dental alveolar ridge. Then, the respective heights of the DH lines for the respective teeth arranged on the plane along a guide line descriptive of the ideal individual dental arch form are adjusted to a predetermined level, followed by adjustment of the angle of inclination of the representative plane for each tooth relative to a facial reference line set up on the face. Accordingly, the dental set-up model can easily be prepared.

If required, the maxillary occlusal plane and the mandibular occlusal plane may be determined within the framework of the electronic data and, based on the occlusal plane so determined, the height of the DH line for each tooth or the angle of inclination of the representative plane for each tooth may be modified. Accordingly, the dental set-up model can easily be prepared.

Also if desired, and particularly when the over-jet and the over-bite between the maxillary anterior teeth and the mandibular anterior teeth exceed respective predetermined value, the respective positions of the maxillary and mandibular anterior teeth are adjusted so that the respective occlusal planes of the maxillary and mandibular dentitions can be determined while they have been adjusted, followed by modification of the height of the DH line for each tooth or the angle of inclination of the representative plane for each tooth. Accordingly, even though malocclusion is found in the patient, the dental set-up model corresponding to the shape of the dentitions and the dental alveolar ridges of the patient can easily prepared.

BRIEF DESCRIPTION OF THE DRAWINGS

In any event, the present invention will become more clearly understood from the following description of a preferred embodiment thereof, when taken in conjunction with the accompanying drawings. However, the embodiment and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 4 is a table showing heights of DH lines;

DETAILED DESCRIPTION OF THE PREFERRED EMBODIMENTS

The present invention will now be described in conjunction with a preferred embodiment thereof with reference to the accompanying drawings.

Figure 1:
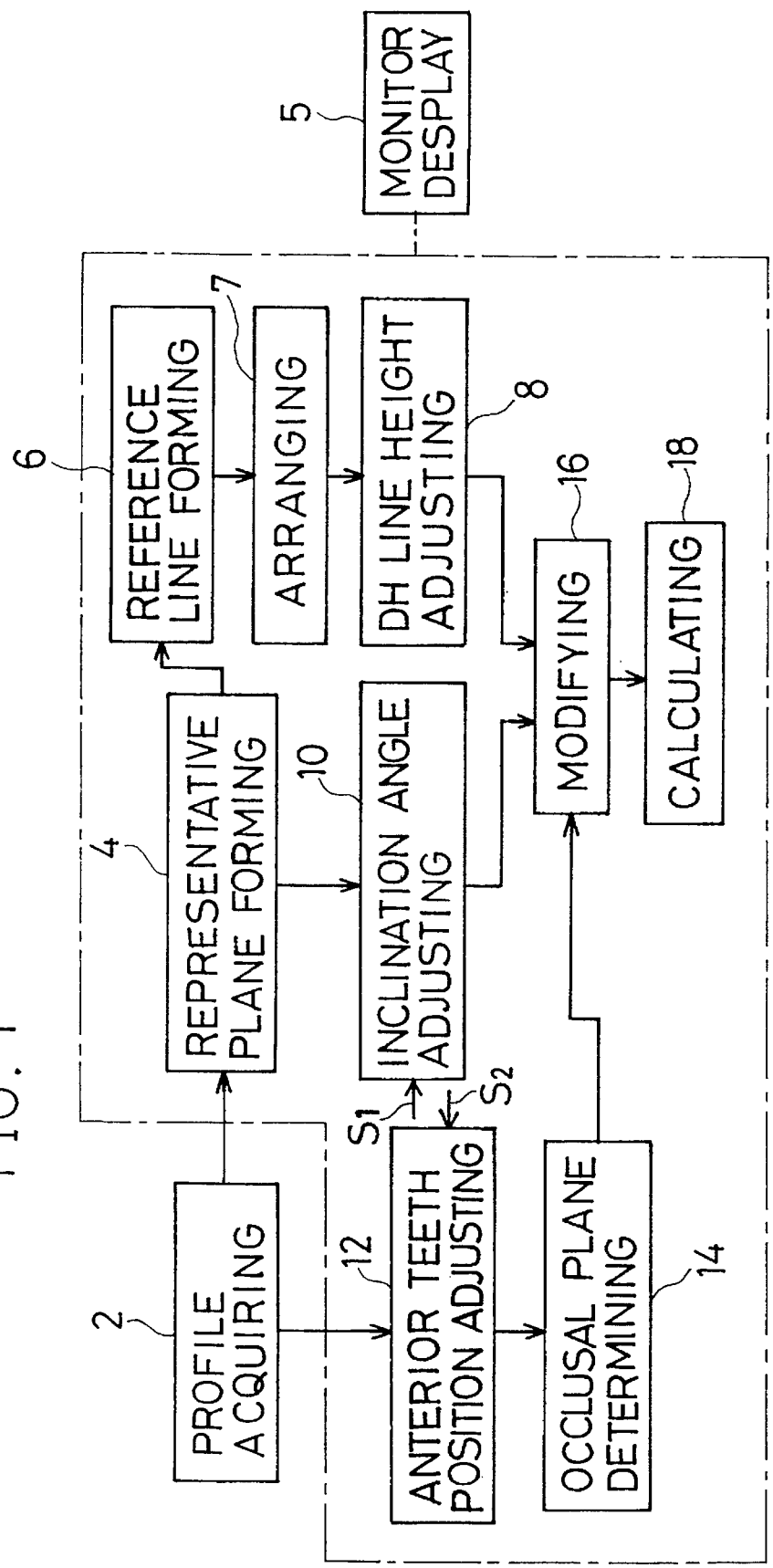
FIG. 1 is a block diagram showing an apparatus for making a dental set-up model according to a preferred embodiment of the present invention.

Referring to FIG. 1, there is shown, in a block circuit diagram, an apparatus for making a dental set-up model according to one embodiment of the present invention. This apparatus includes a profile acquiring means 2 for acquiring electronic data descriptive of the shape of dental teeth and dental alveolar ridges to be orthodontically treated, and an image presenting unit 3 including a monitor display 5 for displaying a three-dimensional image of a dental set-up model that is configured according to predetermined references set up according to the acquired electronic data.

The image presenting unit 3 referred to above includes a representative plane synthesizing means 4 for defining a representative plane for each dental tooth in reference to the anatomical reference point (representative point) on the basis of the shape of the dentition acquired by the profile acquiring means 2; a reference line synthesizing means 6 for defining reference lines (DI and DH lines) for each dental tooth on the basis of the respective representative plane; an arranging means 7 for arranging the DH lines for the respective teeth on a plane along a guide line descriptive of an ideal individual dental arch form: a DH line height adjusting means 8 for adjusting the height of the DH line deemed for each dental tooth to a predetermined level; and an inclination adjusting means 10 adjusting, in response to an inclination adjusting command S 1, the angle of inclination of the respective representative plane for each dental tooth with respect to a facial reference line defined on the face.

The image presenting unit 3 also includes an anterior tooth position adjusting means 12 for properly adjusting, in response to an anterior tooth position adjusting command S2, a displacement between anterior mandibular and maxillary teeth in the event that such displacement exceeds a predetermined value; an occlusal plane determining means 14 for defining the occlusal plane on the basis of the position of the anterior teeth which has been adjusted; a modifying means 16 for modifying the height of the DH line or rectifying the angle of inclination of the representative plane for each dental tooth according to the occlusal plane deemed by the occlusal plane determining means 14; and a calculating means 18 for calculating a displacement between the reference point (representative point) and the reference lines (DI and DH lines) for each dental teeth along the dental alveolar ridge.

The operation of the apparatus of the present invention will now be described.

1. Profile Acquisition

Dental impressions of the maxilla and mandible of a dental patient are prepared in any known manner using a known dental impression material. The profile of a dental impression model which is a replica of the dentition and alveolar ridge both obtained before dental rectification is measured on a non-contact basis by and converted into electronic data by the profile acquiring means 2 which may be a three-dimensional profile analyzer utilizing a beam of irradiation such as, for example, a laser beam. The dental alveolar ridge referred to above is to be understood as including the maxilla or mandible and the membrane. The three-dimensional profile analyzer referred to above and used in the practice of the present invention may be of any known type such as, for example, a multi-exposure high-speed analyzer of a type utilizing a multi-slit laser and a CCD camera or a pattern projecting (beam-traversing) analyzer and, therefore, the details thereof will not be herein discussed for the sake of brevity.

The electronic data are inputted to the image presenting unit 3 so that the model of the original dentition and dental alveolar ridge can be reproduced three-dimensionally on the monitor display 5. This model is utilized to prepare a denture model after having been imparted necessary data on the basis of a predetermined reference set up according to the shape of each dental teeth and modified as hereinafter described.

2. Determination of References

Figure 2:
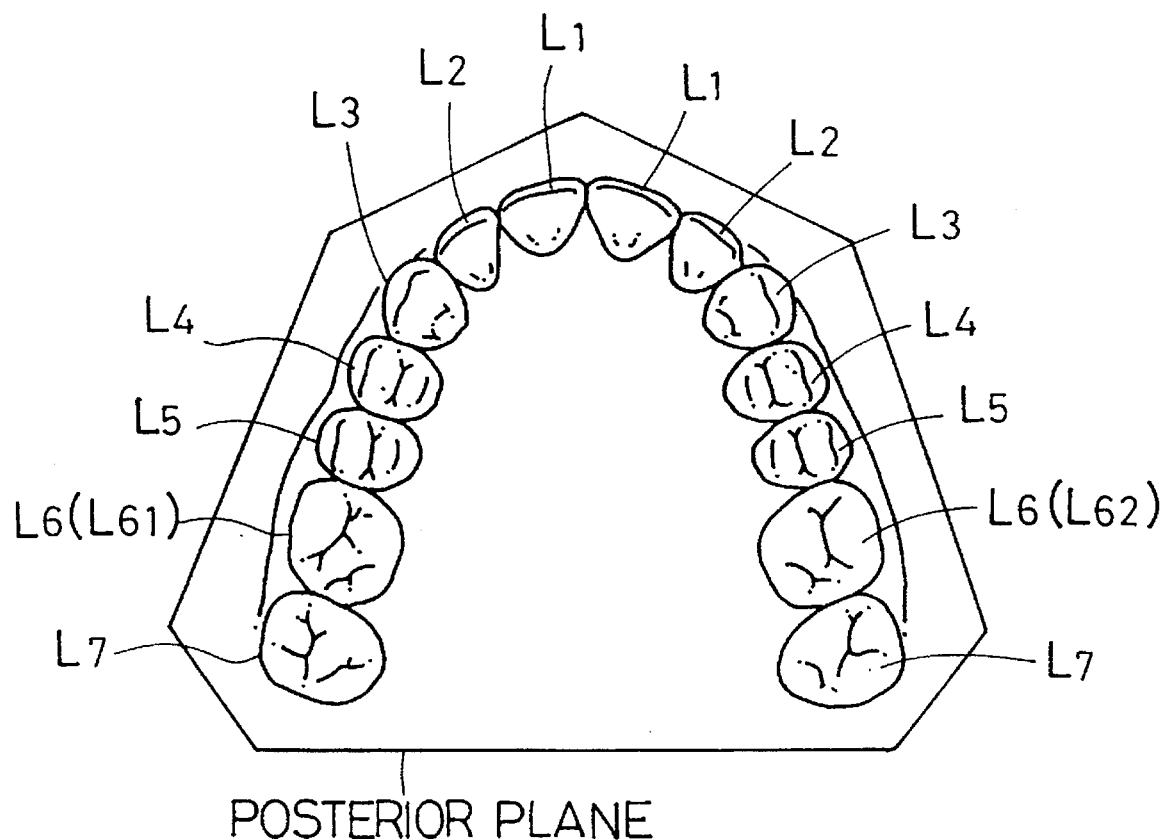
FIG. 2 is a plan view showing schematically a model of dentition.
Figure 2:
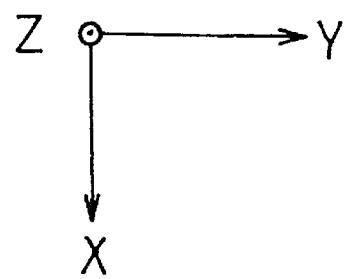

Based on the profile of the dentition and dental alveolar ridge of a dental patient, various planes that are used as references are determined. A model of the mandibular dentition is shown in FIG. 2. In FIG. 2, reference characters L1 to L7 represent numbers given to the respective mandibular teeth, wherein reference character L1 represents central incisors, reference character L2 represents lateral incisors, reference character L3 represents cuspids, reference characters L4 and L5 represent respective bicuspids, and reference characters L6 and L7 represent respective molars. Of the molars, the left first molar and the right first molar are identified by L61 and L62, respectively. For the maxillary dentition, a similar tooth designation is employed, except that in place of the character "L", a character "U" is employed. In FIG. 2, a direction extending from the anterior teeth (for example, the central incisors L1) and perpendicular to the posterior plane of the model is defined as an axis X; a direction extending parallel to the posterior plane of the model is defined as an axis Y; and a direction extending perpendicular to the plane of a sheet of FIG. 2 is defined as an axis Z.

At the outset, initial occlusal planes KH1 are defined. This initial occlusal planes KH1 are an initial virtual plane determined according to the original dentition before dental rectification. So far as the mandible is concerned, the initial occlusal plane KH1 is represented by a plane defined by three representative points lying on the respective cusps or edges of the central incisors and left and right first molars L1, L61 and L62. Similarly, so far as the maxilla is concerned, the initial occlusal plate KH1 is represented by a plane defined by three representative points lying on the respective cusps or edges of the central incisors and left and right first molars U1, U61 and U62. See FIG. 7A. The cusp is a prominence on the coronal occlusal surface of each molar, and the representative point on the cusp is intended to mean a stylo-prominence in the case of the cuspid and a buccal cusp apex in the case of each molar. The edge refers to the incisor edge, and the representative point on the edge is intended to mean an intermediate point of the anterior teeth (central and lateral incisors). Also, based on the profile of the dental alveolar ridge, a dental alveolar ridge plane GH representative of contour data of a plan shape of the dental alveolar ridge is also formed (See FIGS. 3 and 5). Then, the Frankfort horizontal plane FH which represents the facial reference line set at the face is set up (See FIGS. 6 to 8). Where the gnathostatical model is used for the denture model, a plane parallel to the bottom of the modal is used as the Frankfort horizontal plane. In the case of the use of the parallel model, since the occlusal plane lies parallel to the bottom of the model, the Frankfort horizontal plane is determined based on the angle of lateral and anterior-posterior inclination relative to the bottom of the model (the initial occlusal plane).

Figure 3A:
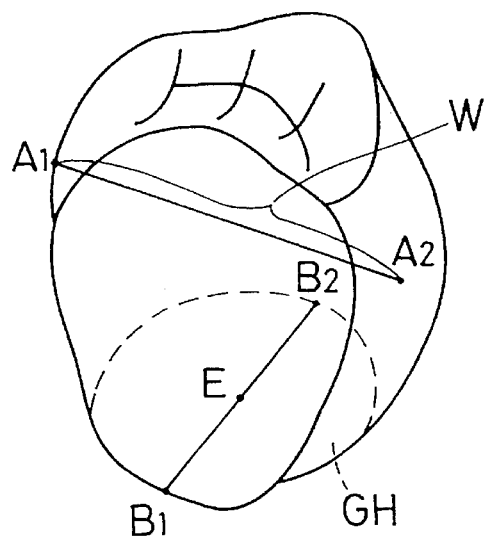
FIGS. 3A to 3D are perspective views showing first to fourth steps of forming reference lines on a three-dimensional model of a tooth, respectively.

FIG. 3A illustrates a three-dimensional model of a tooth displayed on the screen of the monitor display 5. The tooth displayed by the monitor display 5 is the one cut into a polygonal-sectioned columnar shape (for example, a hexagonally-sectioned columnar shape) with the dental alveolar ridge plane GH taken as the bottom of the tooth, said columnar shape having its side face containing at least one of anatomically proximal and distal contact points A1 and A2 and defining a boundary region of the teeth. The contact point referred to above means the point of contact between the neighboring tooth, and the contact point adjacent the -facial median line is referred to as the proximal contact point whereas the contact point remote from the facial median line is referred to as the distal contact point. The anatomically proximal and distal contact points A1 and A2 represent an ideal point at which the neighboring teeth should contact with each other. The distance between these contact points A1 and A2 represents the interdental width W. Also, the bucco-cervical point B1 and the linguo-cervical point B2 are also specified. In general, the buccal side is referred to as the stomatic anterior side while the lingual side is referred to as the stomatic posterior side. The tooth neck is known as a transit between the coronal occlusal surface of tooth and the root of tooth.

Figure 3B:
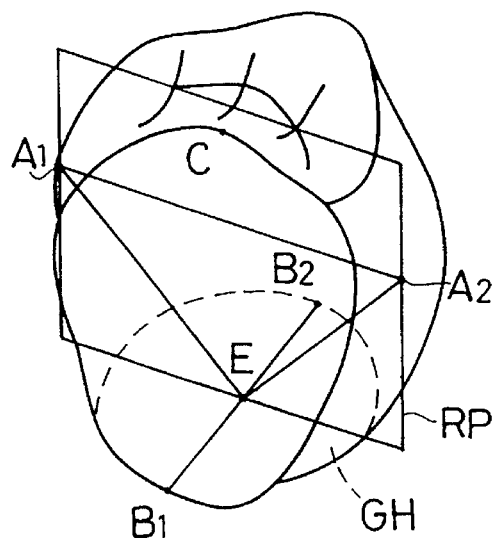
Figure 3C:
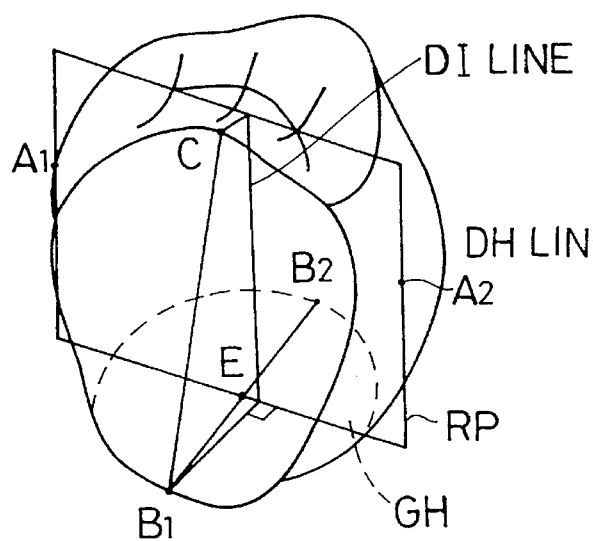
Figure 3D:
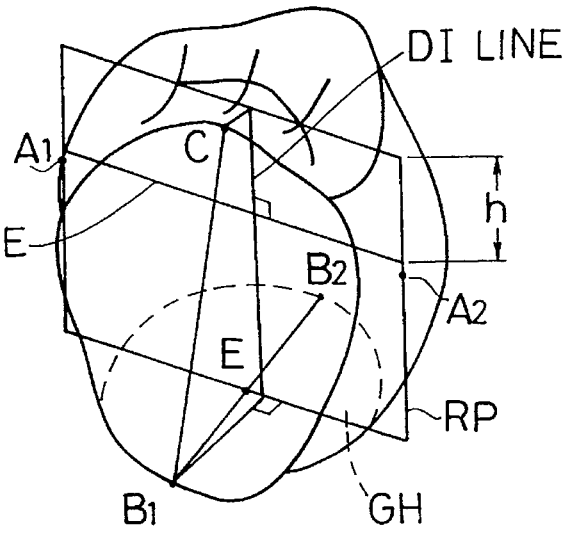

Then, as shown in FIGS. 3B to 3D, for each tooth, a representative plane RP and the DI and DH lines which are used as references in the determination of the tooth shape are defined in reference to the reference points A1, A2, B1 and B2.

2-1. Determination of Representative Planes

At the outset, the representative plane RP is foraged by the representative plane synthesizing means 4. As shown in FIG. 3B, an intermediate point E between the bucco-cervical point B1 and the linguo-cervical point B2 is specified and the representative plane RP is synthesized as defined by the anatomically proximal contact point A1, the anatomically distal contact point A2 and the intermediate point E. This representative plane RP is line-drawn on the monitor display 5, shown in FIG. 1, for each tooth.

2-2. Reference Line Formation

As shown in FIG. 3C, using the reference line synthesizing means 6, the DI line corresponding to the straight line connecting between the bucco-cervical point B1 and the representative point C of the cusp or edge which is projected onto the representative plane RP is formed. Then, as shown in FIG. 3D, the DH line is formed which intersects the DI line perpendicularly at a point spaced a predetermined distance h from the representative point C towards the dental alveolar ridge. As shown in FIG. 4, the predetermined distance h is an empirical value that differs for each tooth, and this distance h may be modified later once it has been used as an initial value. The DI and DH lines are in practice drawn on the screen of the monitor display 5 for each tooth. It is to be noted that the length of the DH line for each tooth represents the interdental width W for each tooth. In this way, references are determined according to the shape of each tooth and, based on these references, the dental set-up model is formed.

3. Model Formation

Figure 5A:
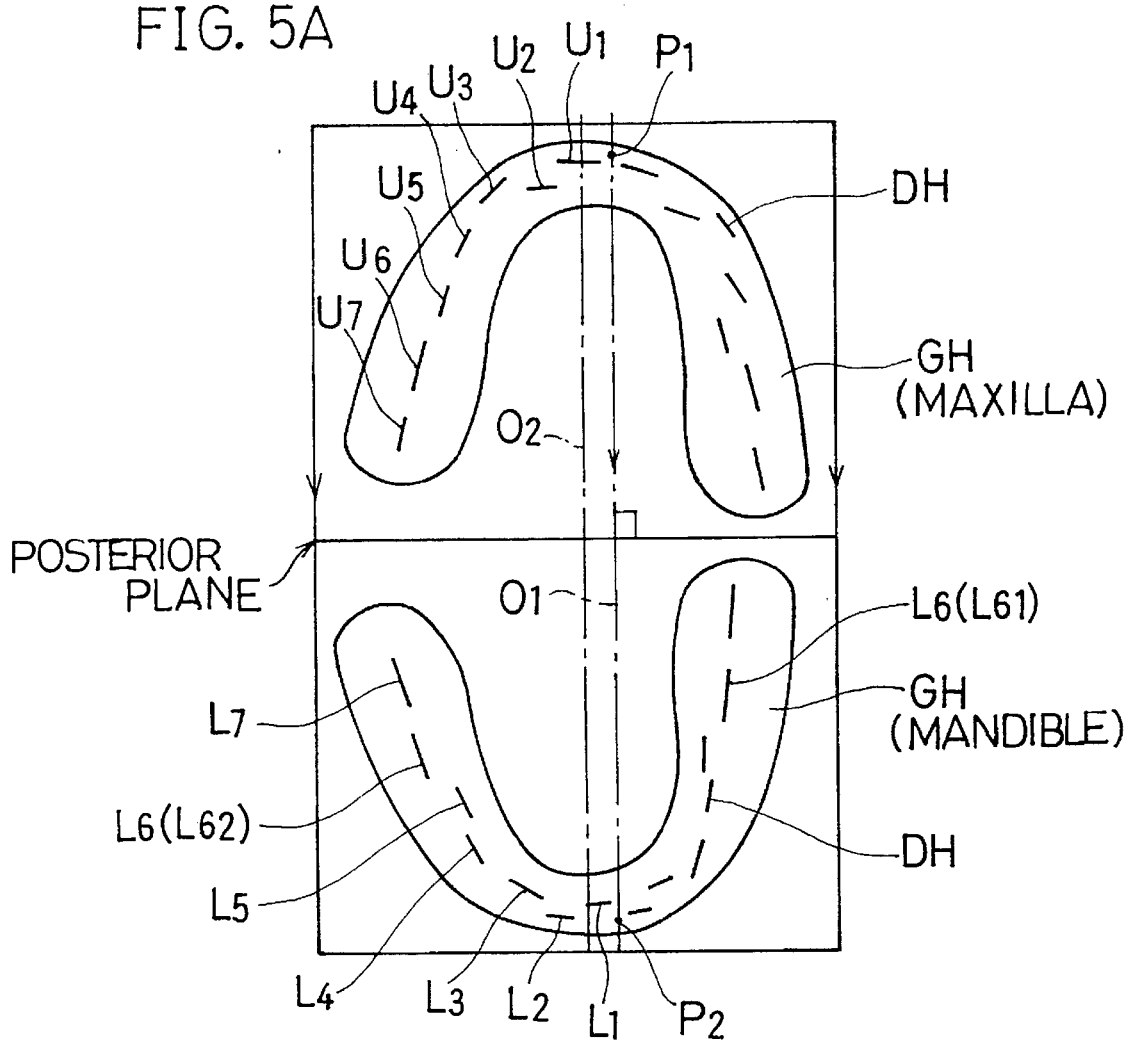
FIG. 5A is a plan view showing maxillary and mandibular teeth before orthodontic treatment that are projected on the plane of a dental alveolar ridge.
Figure 5B:
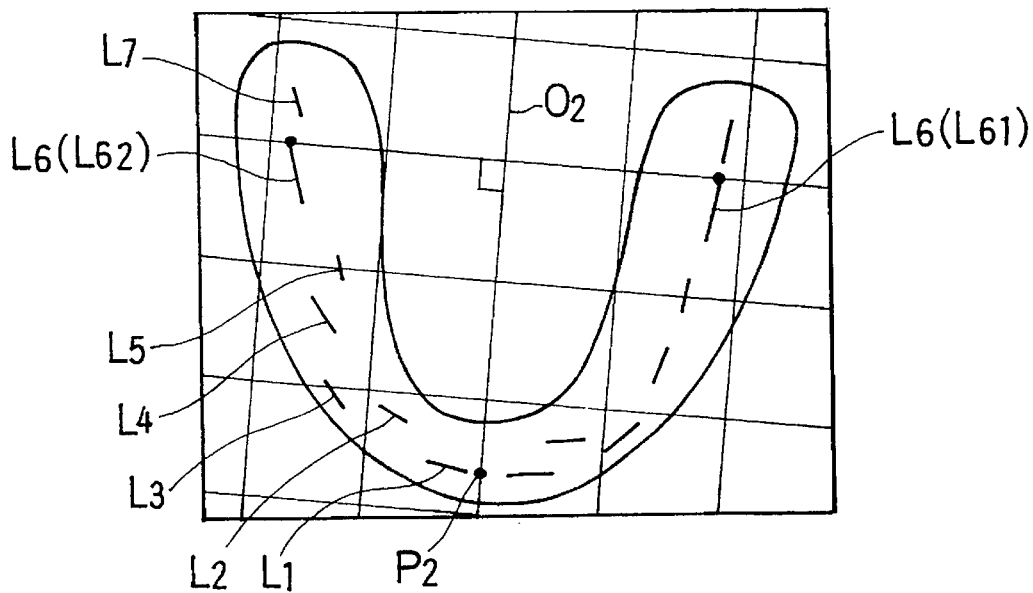
FIG. 5B is a plan view showing a different example of arrangement of the mandibular teeth.

At the outset, center lines which are used as references for the maxilla and the mandible are determined. As shown in FIG. 5A, the DH line for each tooth is presented on the dental alveolar ridge plane GH for each of the maxilla and the mandible on the screen of the monitor display 5. The maxilla and the mandible are displayed in a center spread fashion with respect to the posterior plane of the model. In such case, based on the facial medial line or an X ray photo of the maxilla and mandible, lines 01 and 02 are drawn from the points P1 and P2 in the vicinity of anterior teeth, which are deemed to be respective median center of the maxilla and the mandible, so as to intersect perpendicularly the posterior plane of the model, and the mandibular dental arch is moved to bring the mandibular center line into alignment with the maxilla center line 01. Based on this temporary center line 01, L62 which represents the point of symmetry of the first molar L61 with respect to the facial median line can be determined. Should this L62 displace from the dental alveolar ridge plane GH, the temporary center line 01 is displaced to 02 to bring this L62 onto the dental alveolar ridge plane GH to thereby render the line 02 to be the center line of the maxilla and the mandible. It is, however, to be noted that, in the event that as shown in FIG. 5B the left and right first molars L61 and L62 are inclined relative to the dental alveolar ridge plane GH, the center line 02 need be rotated depending on such inclination. In this way, the final center line 02 is determined.

3-1. Position Adjustment of Anterior Teeth

In the meantime, where a malocclusion is found between the mandibular and maxillary anterior teeth, a displacement, for example, between the tips of the mandibular central incisors L1 and the tips of the maxillary central incisors U1 in the vertical direction is referred to as an over-bite (OB) and that in the horizontal direction is referred to as an over-jet (OJ). A proper over-bite value is about 2 mm and a proper over-jet value is also about 2 mm. In the event that malocclusion of the patient is such that both of the over-bite and over-jet values depart from the respective proper value, orthodontic correction is required to remedy the malocclusion. In such case, the anterior tooth position adjusting means 12 operates in response to the anterior tooth position adjusting command S2 to adjust at least one of the position of the representative point C of the edge of the maxillary anterior teeth and the representative point C of the edge of the mandibular anterior teeth in the following manner so that the maxillary and mandibular anterior teeth may assume respective positions required to satisfy the proper over-jet and over-bite values.

Figure 6A:
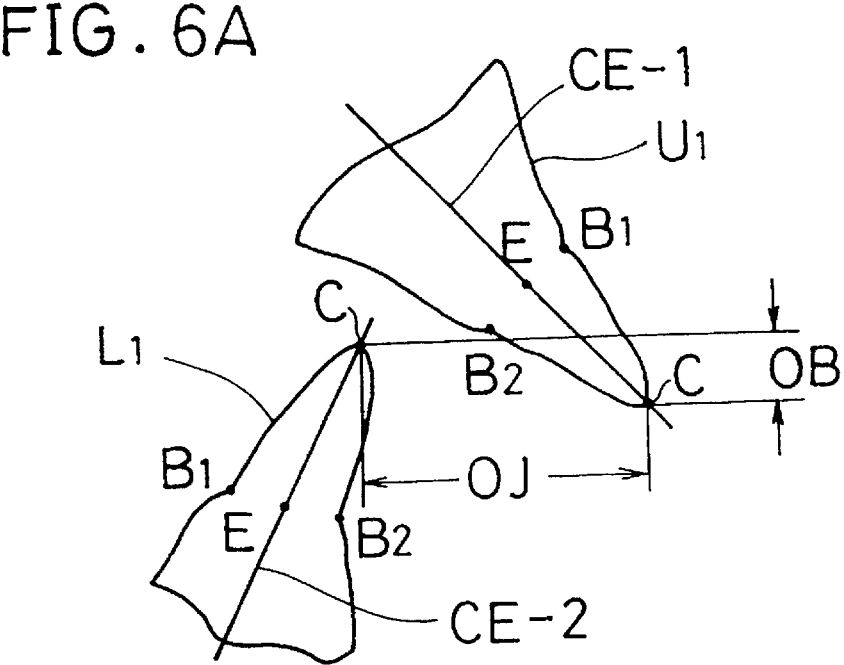
FIG. 6A is a side view showing an over-bite and an over-jet exhibited by the maxillary and mandibular anterior teeth.
Figure 6B:
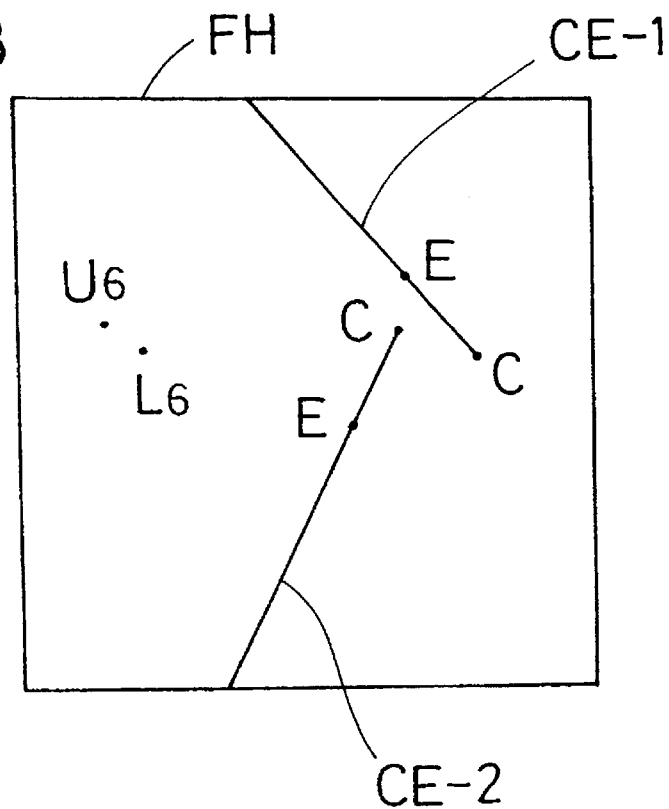
FIG. 6B is a schematic side view of FIG. 6A.

Referring now to FIG. 6A, so far as the maxillary central incisor U1 is concerned, a central contour line including the representative point C of the edge, the bucco-cervical point B1 and the linguo-cervical point B2 and positioned on the center line CE-I that connects between the representative point C of the edge of the maxillary central incisor U1 and the intermediate point E, is depicted. Similarly, a central contour line including the representative point C of the edge, the bucco-cervical point B1 and the linguo-cervical point B2 and positioned on the center line CE-I that connects between the representative point C of the edge of the mandibular central incisor L1 and the intermediate point E, is depicted. As shown in FIG. 6B, the CE-1 and CE-2 lines of the maxillary and mandibular central incisors U1 and L1 are displayed together with the Frankfort horizontal plane on the monitor display 5. In this figure so displayed, the over-bite (OB) value and the over-jet (OJ) value of each of the maxillary and mandibular central incisors U1 and L1 and the angle between the Frankfort horizontal plane FH and each of the CE-1 and CE-2 lines are displayed. Thereafter, based on this displayed figure, the respective positions of the maxillary and mandibular central incisors U1 and L1 are adjusted.

Figure 7A:
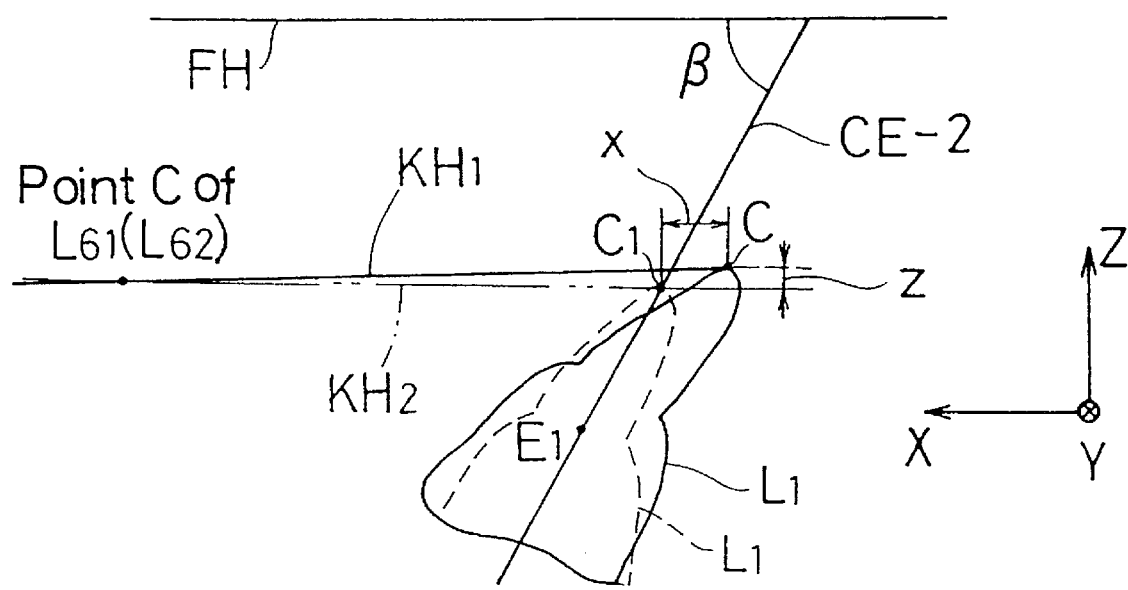
FIG. 7A is a side view showing the mandibular anterior teeth.

Correction of the position of the mandibular central incisor L1 is determined in reference to, for example, an X ray photo of the patient's mandible. In such case, as shown in FIG. 7A, a new representative point C1 displaced x mm in the X-axis direction and z mm in the Z-axis direction from the position of the representative point C of the edge of the central incisor L1 is specified with the mandibular initial occlusal plane KH1 taken as reference. It is to be noted that should the necessity arise, such displacement may occur in the Y-axis direction. Also, the angle β between the CE-2 line of the central incisor L1 and the Frankfort horizontal plane FH is specified. Based on the anterior tooth position adjusting command S2, the position of the mandibular central incisor L1 is determined as shown by the dotted line.

Figure 8A:
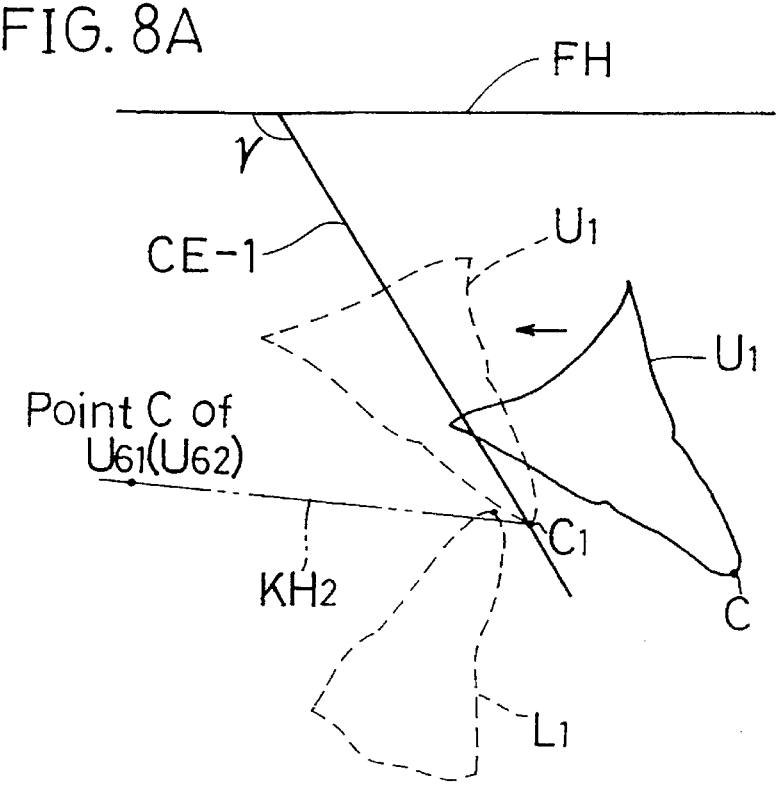
FIG. 8A is a side view showing the maxillary anterior teeth.

Then, the position of the maxillary central incisor U1 is determined. In such case, as shown in FIG. 8A, the point to which the maxillary and mandibular central incisors U1 and L1 are to be moved to attain the proper over-jet (OJ) and over-bite (OB) values are specified and also, the angle γ between the CE-1 line of the maxillary central incisor U1 and the Frankfort horizontal plane FH is specified. At this time, an interference check is made to avoid any possible overlap between respective outer contour lines of the maxillary and mandibular central incisors U1 and L1.

3-2. Determination of Occlusal Plane

Figure 7B:
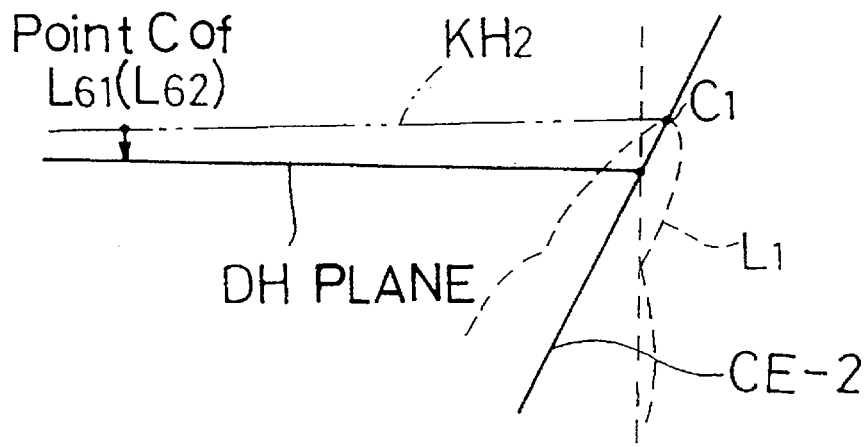
FIG. 7B is a side view showing a method of forming the mandibular DH plane.

As shown in FIG. 7A, in view of the position of the mandibular central incisor L1 being changed to that shown by the dotted line, change is made from the initial occlusal plane KH1 to a new occlusal plane KH2. In other words, the occlusal plane determining means 14 determines the new occlusal plane KH2 of the mandible which is defined by the position at which the representative point C of the edge of the mandibular anterior teeth L1 has been adjusted and the position of the representative point C of the respective cusps of the mandibular left and right first molars L61 and L62 obtained by the profile acquiring means 2. Then, as shown in FIG. 7B, a DH plane of the mandible including the DH lines is determined in reference to the new occlusal plane KH2 of the mandible.

Figure 8B:
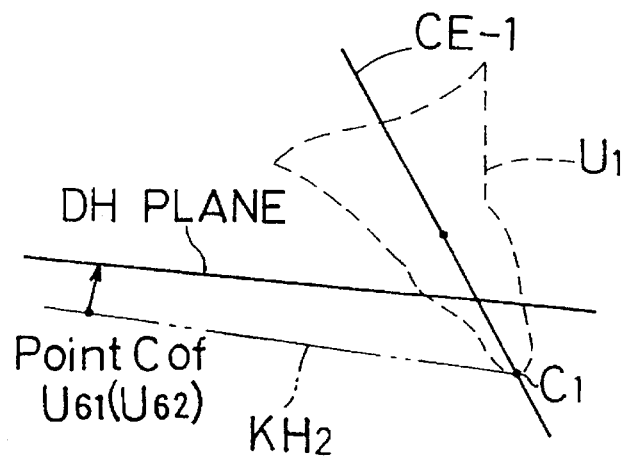
FIG. 8B is a side view showing a method of forming the maxillary DH plane.

Similarly, as shown in FIG. 8A, when the position of the maxillary central incisor U1 is changed to the position shown by the dotted line, it is changed to a new maxillary occlusal plane KH2. In other words, the occlusal plane determining means 14 determines the new occlusal plane KH2 of the maxilla which is defined by the position at which the representative point C of the edge of the maxillary anterior teeth U1 has been adjusted and the position of the representative point C of the respective cusps of the maxillary left and right first molars U61 and U62 obtained by the profile acquiring means 2. Then, as shown in FIG. 8B, a plane of the maxilla including the DH lines is determined in reference to the new occlusal plane KH2 of the maxilla.

In this way, the new occlusal planes KH2 of the maxilla and mandible are determined. Nevertheless, if the over-bite and over-jet values of the maxillary and mandibular anterior teeth before orthodontic rectification are proper, no position of any of the anterior teeth is adjusted and the initial occlusal planes KH1 are retained.

It is to be noted that, where no position of the maxillary and mandibular anterior teeth need be adjusted and the respective positions of the left and right first molars L61 and L62 are required to be adjusted, a new occlusal plane KH2 is determined upon change of such positions and the DH plane is determined for each of the maxilla and the mandible.

Also, if there is a tooth to be removed, the number L1 to L7 and U1 to U7 of such tooth is specified. In addition, if a tooth has been removed, a space for a denture tooth is secured.

3-3. Arrangement

Figure 9A:
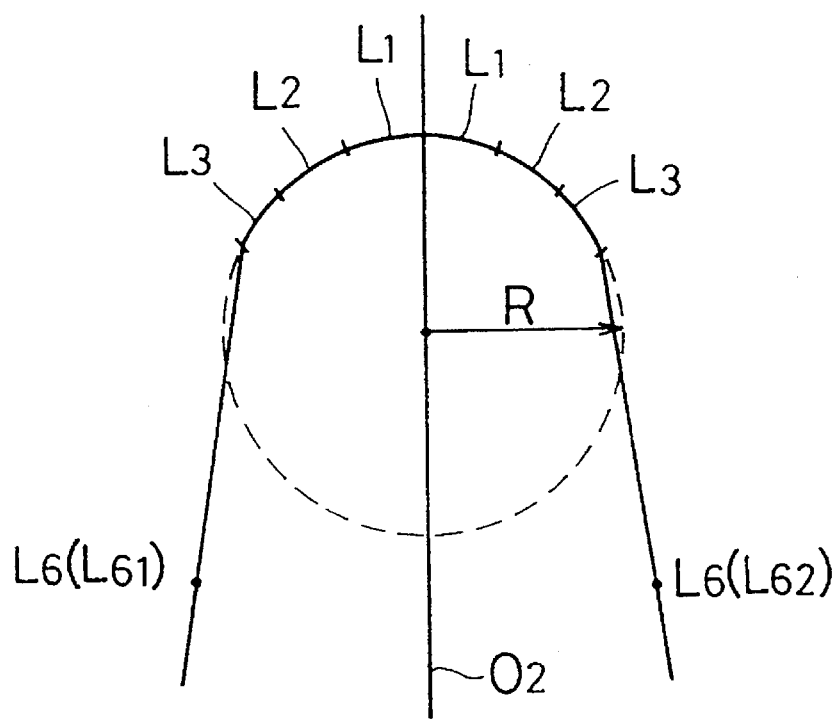
FIG. 9A is a plan view showing a method of forming guide lines descriptive of an ideal individual dental arch form.
Figure 9B:
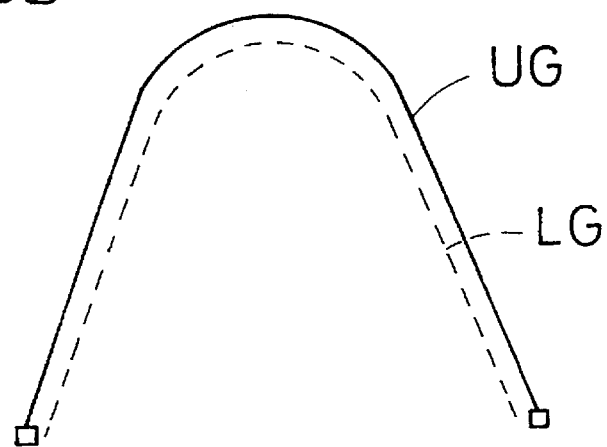
FIG. 9B is a plan view showing the guide lines formed.
Figure 10:
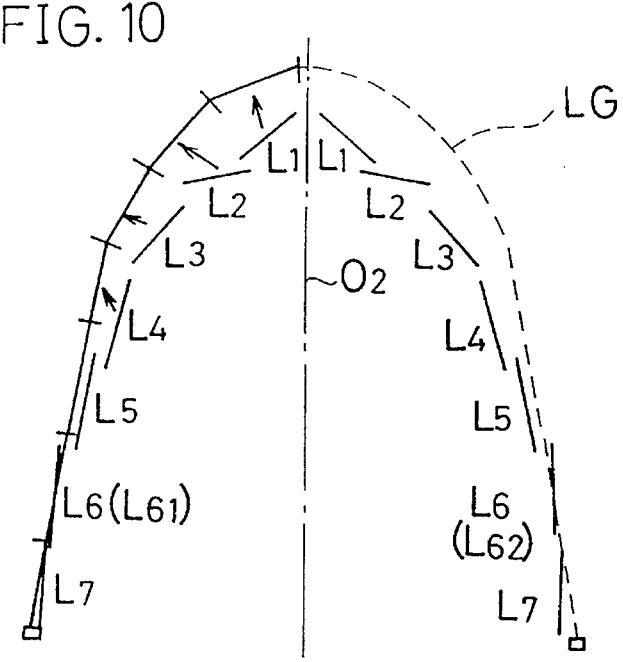
FIG. 10 is a plan view showing the dentition.

Then, in order to arrange the dental DH line, a guide line representative of the plane configuration of the ideal individual dental arch form is determined. In the first place, an arc for arranging the DH lines of the anterior teeth is determined. FIG. 9A illustrates, as an representative, the mandible, and using as a radius R of arc the sum of the respective lengths (interdental widths) W of the DH lines of the central incisor L1, lateral incisor L2 and cuspid L3 on one side, a circle is depicted on the center line 02 so as to pass through the respective center points P of the maxillary and mandibular anterior teeth. The respective DH lines of the central incisors L1, lateral incisors L2 and cuspids L3 on both sides are placed along this circle, and the terminuses of the DH lines of the cuspids L3 and the left and right first molar L61 and L62 are connected with each other by means of respective straight lines. A similar guide line is prepared for the maxilla. The guide lines UG and LG so prepared for the maxilla and the mandible, respectively, are, as shown in FIG. 9B, overlapped with each other so that interference between the lines are checked. In this figure, the guide line UG for the maxilla is shown by the solid line while the guide line LG for the mandible is shown by the broken line. After the interference checking, final guide lines are determined.

As described above, by replacing the individual teeth with the DH lines and arranging them on the guide line LG (UG), an accurate arrangement of the teeth is possible in a short time. Also, the amount of data associated with the arrangement is only that of the DH line data which is small as compared with the amount of the three-dimensional shape data.

3-4. DH Line Height Adjustment

Figure 11:
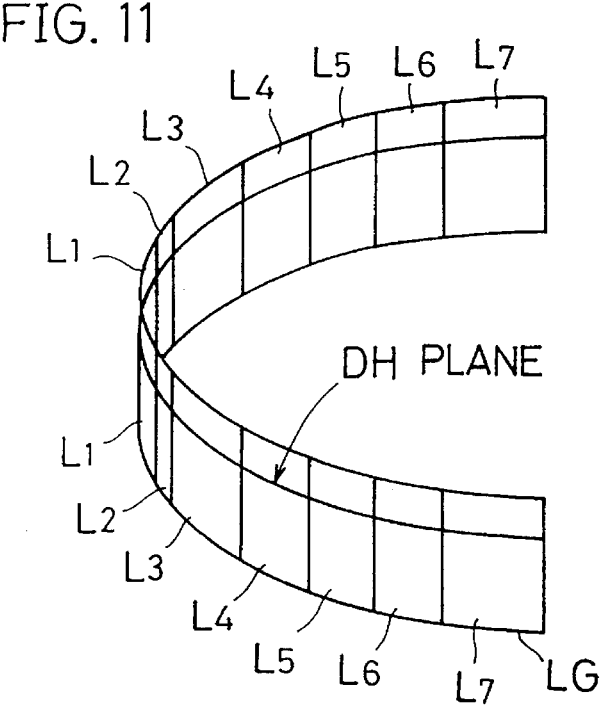
FIG. 11 is a perspective view showing a condition in which the DH line for each tooth has been adjusted to a predetermined level.

The height of the DH line for each of the teeth laid on a plane along the guide line LG for the mandible as shown in FIG. 11 is adjusted by the DH line height adjusting means 8 to a predetermined level. This height corresponds to the height of the previously discussed DH plane. As described above, where the occlusal planes of the maxilla and the mandible have been changed, the height of the DH plane is modified by the modifying means 16. Also, for the maxilla the height of the DH line is adjusted in a similar manner.

3-5. Adjustment of Inclination Angle

Figure 12:
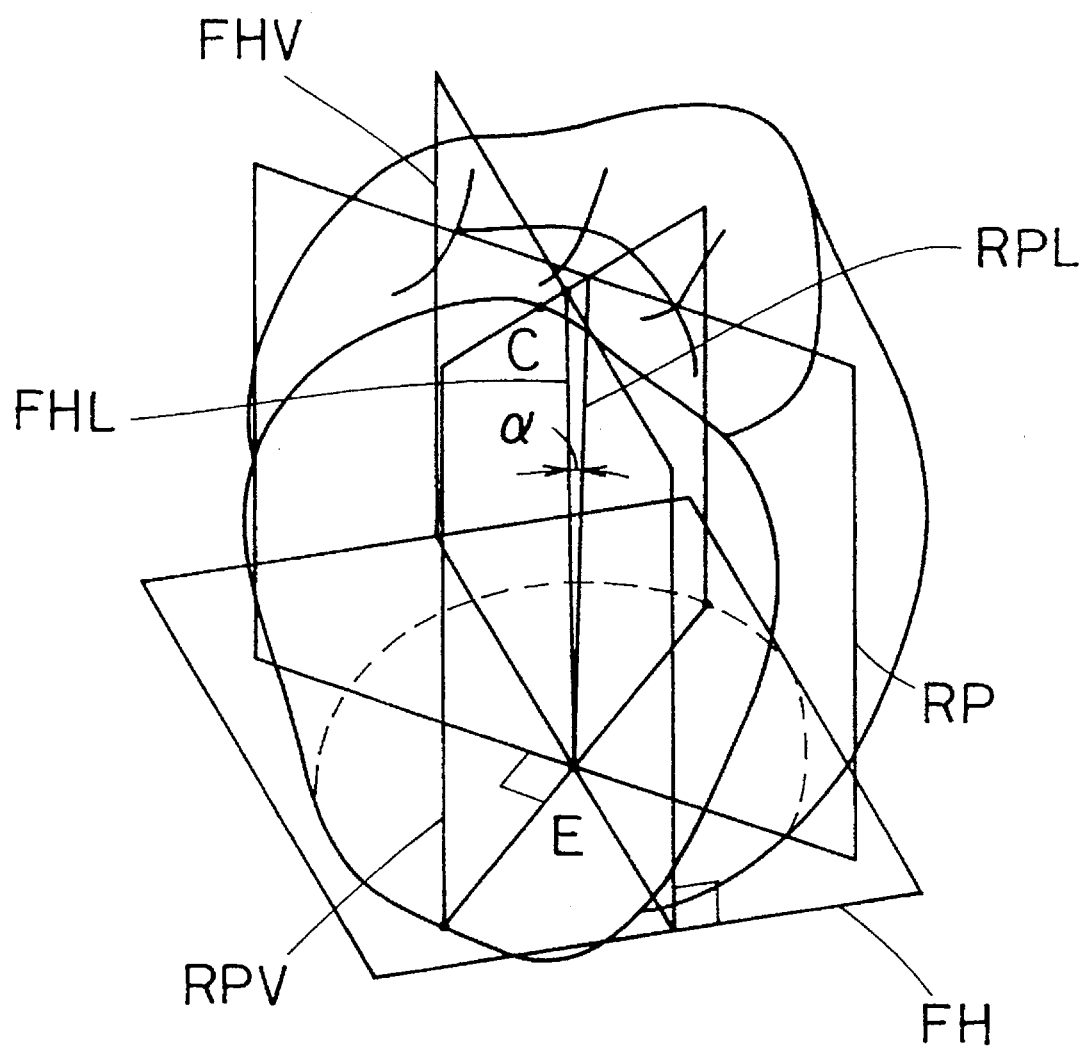
FIG. 12 is a perspective view showing the angle of inclination of each tooth.

The angle of inclination of each tooth is adjusted by the inclination angle adjusting means 10. As shown in FIG. 12, the angle α of inclination is intended to mean the angle formed by the straight line RPL at which the representative plane RP of the respective tooth intersects the vertical plane RPV thereof including the intermediate point E, relative to the straight line FHL at which the vertical plane RPV intersects the vertical plane FHV set vertical to the cranial reference line (Frankfort horizontal plane) defined in the face and including the intermediate point E. For each tooth, a target correction value to be corrected is predetermined relative to the angle α of inclination before correction. In response to the inclination angle adjusting command S1 which is outputted according to the target correction value, the inclination angle adjusting means 10 adjusts the angle α of inclination of each tooth so that the angle of inclination attains the target correction value. Similarly, in the case where the maxillary and mandibular occlusal planes have been changed, the angle α of inclination of the representative plane RP of each tooth is modified by the modifying means 16.

3-6. Formation of Three-Dimensional Profile

Where determination of the maxillary and mandibular occlusal planes is difficult with the arrangement of the DH lines of each tooth, a three-dimensional shape obtained in the manner as discussed under the heading "1. Profile Acquisition" is imparted to the individual teeth so arranged in the manner as discussed under the heading "3-3. Arrangement" so that the three-dimensional arrangement of the teeth is formed on the screen of the monitor display 5.

3-7. Confirmation of Occlusal Position

On the monitor display 5, the maxillary and mandibular teeth having the three-dimensional shape are allowed to bite so that the areas of contact between the maxillary and mandibular teeth are determined and, based on the areas of contact between the maxillary and mandibular teeth the occlusal condition can be confirmed. If the necessity arises at this time, re-arrangement of the individual teeth may be carded out so that the contact area for each tooth can be minimized.

3-8. Movement of Dental Arch

Should it be determined according to a confirmation of the occlusal position that no proper occlusal relationship is obtained between the maxilla and the mandible, it may be contemplated to move three-dimensionally the mandibular dental arch on the screen of the monitor display 5 until the proper occlusal relationship is obtained (This movement may include leftward or rightward movement of the mandibular dental arch under "3. Model Formation"). This movement is a simulation of a surgical orthodontics.

It is to be noted that a displacement on the dental alveolar ridge between the reference points (representative points) of the teeth, including the anatomically proximal contact point A1, the anatomically distal contact point A2, the bucco-cervical point B1 and the linguo-cervical point B2 or the representative point C of the cusp (edge), and the reference lines of the teeth including the above described adjusted DI line or the DH line is calculated for each tooth by the calculating means 18. This displacement is indicative of the profile of the dental set-up model. Also, the amount of movement of the mandibular dental arch during the step of moving the dental arch is also calculated. In this way, the dental set-up model is converted into data.

Thus, on the screen of the display monitor 5, the dental set-up model for use in the practice of dental treatment can be prepared.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. For example, although in the illustrated embodiment it has been described that the set-up model is intended for use in orthodontics, it may be used for preparing a denture based on data associated with each tooth stored in a data base.

Accordingly, such changes and modifications are, unless they depart from the scope of the present invention as delivered from the claims annexed hereto, to be construed as included therein.

What is claimed is:

1. A method of making a dental set-up model which comprises:

a profile acquiring step of acquiring electronic data by determining on a non-contact basis a shape of an impression model, which is a replica of dental teeth and dental alveolar ridges of a patient by the use of a three-dimensional profile analyzer utilizing an irradiation beam, said electronic data being descriptive of the shape of the dental teeth and dental alveolar ridges;

a representative plane forming step of forming representative planes by cutting out the individual teeth, within the framework of the electronic data, said representative planes being defined by anatomically proximal contact points A1, anatomically distal contact points A2 and an intermediate point E between a bucco-cervical point B1 and a linguo-cervical point B2;

a reference line forming step of forming, for each tooth, a DI line, which is a straight line connecting between the bucco-cervical point B1 and a representative point C of a cusp or edge that has been projected onto the representative plane, and a DH line intersecting the DI line perpendicularly at a point spaced a predetermined distance from the representative point C towards the dental alveolar ridge;

an arranging step of arranging the DH lines for the respective teeth on a plane along a guide line descriptive of an ideal individual dental arch form;

a DH line height adjusting step of adjusting respective heights of the DH lines for all teeth which have been lined up to a predetermined height; and an inclination angle adjusting step of adjusting an angle of inclination of the representative plane for each tooth relative to a facial reference line set up on the face.

2. The method as claimed in claim 1, further comprising an occlusal plane determining step of determining a maxillary occlusal plane defined by a position of the representative point C of maxillary anterior teeth and a position of the representative point C of left and right maxillary first molars which was obtained during the profile acquiring step and, also, a mandibular occlusal plane deemed by a position of the representative point C of mandibular anterior teeth and a position of the representative point C of left and right mandibular first molars which was obtained during the profile acquiring step, and a modifying step of modifying the height of the DH line for each tooth or an angle of inclination of the representative plane for each tooth, said occlusal plane determining step and said modifying step being performed successively subsequent to the inclination angle adjusting step.

3. The method as claimed in claim 1, further comprising an anterior teeth position adjusting step of adjusting at least one of a position of the representative point C of the maxillary anterior teeth and a position of the representative point C of the mandibular anterior teeth so that a predetermined over-jet value and a predetermined over-bite value are established between the maxillary anterior teeth and the mandibular anterior teeth, an occlusal plane determining step of determining a maxillary occlusal plane, deemed by the position to which the representative point C of the maxillary anterior teeth has been adjusted and respective positions of the representative points C of the left and right maxillary first molars obtained during the profile acquiring step, and a mandibular occlusal plane, deemed by the position to which the representative point C of the mandibular anterior teeth has been adjusted and respective positions of the representative points C of the left and right mandibular first molars obtained during the profile acquiring step, and a modifying step of modifying the height of the DH line for each tooth or the angle of inclination of the representative plane for each tooth on the basis of the maxillary and mandibular occlusal planes so determined, said anterior teeth position adjusting step, said occlusal plane determining step and said modifying step being successively performed subsequent to the inclination angle adjusting step.

4. The method as claimed in claim 1, further comprising a calculating step of calculating a displacement on the dental alveolar ridge between the representative point of each tooth including said points A1, A2, B1 and B2 or C and a reference line of each tooth including said adjusted DI or DH line, said calculating step being perforated subsequent to the inclination angle adjusting step.

5. The method as claimed in claim 1, further comprising a three-dimensional profile forming step of imparting a three-dimensional shape, obtained during the shape acquiring step, to each of the teeth arranged during the arranging step, to thereby form an arrangement of the three-dimensional profile, said three-dimensional profile forming step being performed subsequent to the inclination angle adjusting step.

6. The method as claimed in claim 5, further comprising a confirmation step of occlusal position of confirming an occlusal condition in reference to an area of contact between the maxillary and mandibular teeth by causing the maxillary and mandibular teeth having the three-dimensional shape to bite, said confirmation step of occlusal position being performed subsequent to the three-dimensional profile forming step.

7. The method as claimed in claim 6, further comprising a dental arch moving step of moving the mandibular dental arch so as to attain a proper occlusal relationship between the maxillary and mandibular teeth and calculating the amount of such movement, said dental arch moving step being performed subsequent to the confirmation step of occlusal position.

8. An apparatus for making a dental set-up model which comprises:

a profile acquiring means for acquiring electronic data by determining on a non-contact basis a shape of an impression model, which is a replica of dental teeth and dental alveolar ridges of a patient by the use of a three-dimensional profile analyzer utilizing an irradiation beam, said electronic data being descriptive of the shape of the dental teeth and dental alveolar ridges;

a representative plane forming means for forming representative planes by cutting out the individual teeth, within the framework of the electronic data, said representative planes being defined by anatomically proximal contact points A1, anatomically distal contact points A2 and an intermediate point E between a bucco-cervical point B1 and a linguo-cervical point B2;

a reference line forming means for forming, for each tooth, a DI line, which is a straight line connecting between the bucco-cervical point B1 and a representative point C of a cusp or edge that has been projected onto the representative plane, and a DH line intersecting the DI line perpendicularly at a point spaced a predetermined distance from the representative point C towards the dental alveolar ridge;

an arranging means for arranging the DH lines for the respective teeth on a plane along a guide line descriptive of an ideal individual dental arch form;

a DH line height adjusting means for adjusting respective heights of the DH lines for all teeth which have been lined up to a predetermined height; and an inclination angle adjusting means for adjusting an angle of inclination of the representative plane for each tooth relative to a facial reference line set up on the face.

9. The apparatus as claimed in claim 8, further comprising an occlusal plane determining means for determining a maxillary occlusal plane defined by a position of the representative point C of maxillary anterior teeth and a position of the representative point C of left and right maxillary first molars which was obtained by the profile acquiring means and, also, a mandibular occlusal plane defined by a position of the representative point C of mandibular anterior teeth and a position of the representative point C of left and right mandibular first molars which was obtained by the profile acquiring means, and a modifying means for modifying the height of the DH line for each tooth and an angle of inclination of the representative plane for each tooth.

10. The apparatus as claimed in claim 8, further comprising an anterior teeth position adjusting means for adjusting at least one of a position of the representative point C of the maxillary anterior teeth and a position of the representative point C of the mandibular anterior teeth so that a predetermined over-jet value and a predetermined over-bite value are established between the maxillary anterior teeth and the mandibular anterior teeth, an occlusal plane determining means for determining a maxillary occlusal plane, defined by the position to which the representative point C of the maxillary anterior teeth has been adjusted and respective positions of the representative points C of the left and right maxillary first molars obtained by the profile acquiring means, and a mandibular occlusal plane, defined by the position to which the representative point C of the mandibular anterior teeth has been adjusted and respective positions of the representative points C of the left and right mandibular first molars obtained by the profile acquiring means, and a modifying means for modifying the height of the DH line for each tooth or the angle of inclination of the representative plane for each tooth on the basis of the maxillary and mandibular occlusal planes so determined.

11. The apparatus as claimed in claim 8, further comprising a calculating means for calculating a displacement on the dental alveolar ridge between the representative point of each tooth including said points A1, A2, B1 and B2 or C and a reference line of each tooth including said adjusted DI or DH line.

* * * * *

UNITED STATES PATENT AND TRADEMARK OFFICE
CERTIFICATE OF CORRECTION

PATENT NO. : 5,605,459
DATED : February 25, 1997
INVENTOR(S) : Takayuki Kuroda, Nobuyoshi Motohashi and Mutsushi Muramoto It is certified that error appears in the above-indentified patent and that said Letters Patent is hereby corrected as shown below:

In claim 2, line 31; claim 3, line 52; and claim 3, line 58, correct "deemed" to ---defined---.

In claim 4, line 10, correct "perforated" to ---performed---.

In claim 10, line 1, correct "claimed m" to ---claimed in---.

Signed and Sealed this

First Day of July, 1997

Attest:

*Attesting Officer*

BRUCE LEHMAN
*Commissioner of Patents and Trademarks*